(12) United States Patent
Millard et al.

(10) Patent No.: US 10,320,023 B2
(45) Date of Patent: Jun. 11, 2019

(54) NEAT METHODS FOR FORMING TITANIUM CATECHOLATE COMPLEXES AND ASSOCIATED COMPOSITIONS

(71) Applicant: LOCKHEED MARTIN ADVANCED ENERGY STORAGE, LLC, Bethesda, MD (US)

(72) Inventors: Matthew Millard, Cambridge, MA (US); Emily Grace Nelson, Watertown, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 130 days.

(21) Appl. No.: 15/435,235

(22) Filed: Feb. 16, 2017

(65) Prior Publication Data

US 2018/0233762 A1    Aug. 16, 2018

(51) Int. Cl.
  *C07F 7/28*    (2006.01)
  *H01M 8/18*    (2006.01)

(52) U.S. Cl.
  CPC ............... *H01M 8/188* (2013.01); *C07F 7/28* (2013.01); *H01M 2300/0002* (2013.01); *Y02E 60/528* (2013.01)

(58) Field of Classification Search
  CPC ..................................................... C07F 7/28
  See application file for complete search history.

(56) References Cited

U.S. PATENT DOCUMENTS

| 1,279,295 A | 9/1918 | Downs |
| 2,353,782 A | 7/1944 | Neumark |
| (Continued) | | |

FOREIGN PATENT DOCUMENTS

| CN | 1284208 A | 2/2001 |
| CN | 101877412 A | 11/2010 |
| (Continued) | | |

OTHER PUBLICATIONS

Broere et al "New avenues for ligand-mediated processes . . . ", Chem. Soc. Rev., 2015, 44, 6886. (Year: 2015).*

(Continued)

*Primary Examiner* — Mark Kopec
(74) *Attorney, Agent, or Firm* — BakerHostetler

(57) ABSTRACT

Titanium catecholate complexes can be desirable active materials for flow batteries and other electrochemical energy storage systems, particularly when incorporated in aqueous electrolyte solutions. It can be desirable to avoid introducing even traces of certain organic solvents into aqueous electrolyte solutions. Neat methods for synthesizing titanium catecholate complexes can help avoid the unwanted introduction of trace organic solvents into aqueous electrolyte solutions and also provide further advantages. Methods for synthesizing titanium catecholate complexes can include: combining a catechol compound and a titanium reagent in an absence of solvent to produce a reaction mixture, and reacting the titanium reagent with the catechol compound in a neat state to form a titanium catecholate complex containing at least one catecholate ligand. The titanium catecholate complex can be further reacted with a base to produce a salt form titanium catecholate complex, which can be present in an aqueous phase.

22 Claims, 1 Drawing Sheet

(56) References Cited

U.S. PATENT DOCUMENTS

| | | | |
|---|---|---|---|
| 2,415,792 A | 2/1947 | Gravell |
| 3,294,588 A | 12/1966 | Morton |
| 3,425,796 A | 2/1969 | Bauer |
| 3,428,654 A | 2/1969 | Rubinfeld |
| 3,573,984 A | 4/1971 | Shah |
| 3,707,449 A | 12/1972 | Reinhardt et al. |
| 3,772,379 A | 11/1973 | Woodgate |
| 3,876,435 A | 4/1975 | Dollman |
| 3,916,004 A | 10/1975 | Okada et al. |
| 3,919,000 A | 11/1975 | Yarrington |
| 3,920,756 A | 11/1975 | Tahara et al. |
| 3,929,506 A | 12/1975 | Leddy et al. |
| 3,985,517 A | 10/1976 | Johnson |
| 3,985,585 A | 10/1976 | Tuttle et al. |
| 4,046,861 A | 9/1977 | Reinhardt et al. |
| 4,064,324 A | 12/1977 | Eustace |
| 4,069,371 A | 1/1978 | Zito |
| 4,126,529 A | 11/1978 | DeBerry |
| 4,180,623 A | 12/1979 | Adams |
| 4,202,799 A | 5/1980 | Yoshimura et al. |
| 4,233,144 A | 11/1980 | Pace et al. |
| 4,362,791 A | 12/1982 | Kaneko et al. |
| 4,378,995 A | 4/1983 | Gratzfeld et al. |
| 4,410,606 A | 10/1983 | Loutfy et al. |
| 4,436,711 A | 3/1984 | Olson |
| 4,436,712 A | 3/1984 | Olson |
| 4,436,713 A | 3/1984 | Olson |
| 4,436,714 A | 3/1984 | Olson |
| 4,443,423 A | 4/1984 | Olson |
| 4,443,424 A | 4/1984 | Olson |
| 4,452,914 A * | 6/1984 | Coleman, III ............ C07F 7/28  502/122 |
| 4,468,441 A | 8/1984 | D'Agostino et al. |
| 4,485,154 A | 11/1984 | Remick et al. |
| 4,520,083 A | 5/1985 | Prater et al. |
| 4,563,403 A | 1/1986 | Julian |
| 4,592,973 A | 6/1986 | Pemsler et al. |
| 4,617,244 A | 10/1986 | Greene |
| 4,680,308 A | 7/1987 | Schwartz et al. |
| 4,818,646 A | 4/1989 | Takakubo et al. |
| 4,880,758 A | 11/1989 | Heistand, II et al. |
| 4,952,289 A | 8/1990 | Ciccone et al. |
| 4,959,135 A | 9/1990 | Zenner et al. |
| 4,973,720 A | 11/1990 | Saito et al. |
| 5,084,533 A | 1/1992 | Shah et al. |
| 5,122,461 A | 6/1992 | Hsiung et al. |
| 5,264,097 A | 11/1993 | Vaughan |
| 5,302,481 A | 4/1994 | Ong |
| 5,318,865 A | 6/1994 | Kaneko et al. |
| 5,433,934 A | 7/1995 | Chang et al. |
| 5,472,807 A | 12/1995 | Licht et al. |
| 5,643,670 A | 7/1997 | Chung |
| 5,679,239 A | 10/1997 | Blum et al. |
| 5,759,711 A | 6/1998 | Miyabayashi et al. |
| 5,785,841 A | 7/1998 | Tseng |
| 5,876,581 A | 3/1999 | Itaya et al. |
| 5,910,366 A | 6/1999 | Chowdhury et al. |
| 6,001,326 A | 12/1999 | Kim et al. |
| 6,030,517 A | 2/2000 | Lincot et al. |
| 6,054,230 A | 4/2000 | Kato |
| 6,461,772 B1 | 10/2002 | Miyake et al. |
| 6,475,661 B1 | 11/2002 | Pellegri et al. |
| 6,485,868 B1 | 11/2002 | Tsujioka et al. |
| 6,555,989 B1 | 4/2003 | Pearson |
| 6,585,951 B1 | 7/2003 | Hong et al. |
| 6,624,328 B1 | 9/2003 | Guerra |
| 7,046,418 B2 | 5/2006 | Lin et al. |
| 7,193,764 B2 | 3/2007 | Lin et al. |
| 7,223,833 B1 | 5/2007 | Nielsen et al. |
| 7,252,905 B2 | 8/2007 | Clarke et al. |
| 7,265,162 B2 | 9/2007 | Yandrasits et al. |
| 7,348,088 B2 | 3/2008 | Hamrock et al. |
| 7,463,917 B2 | 12/2008 | Martinez |
| 7,508,568 B2 | 3/2009 | Lin et al. |
| 7,550,231 B2 | 6/2009 | Stauffer |
| 7,557,164 B2 | 7/2009 | Felix et al. |
| 7,625,663 B2 | 12/2009 | Clarke et al. |
| 7,645,540 B2 | 1/2010 | Boone et al. |
| 7,678,728 B2 | 3/2010 | Olson et al. |
| 7,745,056 B2 | 6/2010 | Lee et al. |
| 7,767,777 B2 | 8/2010 | Buesing et al. |
| 7,927,731 B2 | 4/2011 | Sahu |
| 7,931,981 B2 | 4/2011 | Boone et al. |
| 7,935,366 B2 | 5/2011 | Pahuja et al. |
| 7,998,335 B2 | 8/2011 | Feeney et al. |
| 8,129,554 B2 | 3/2012 | Schwaiger |
| 8,187,441 B2 | 5/2012 | Evans et al. |
| 8,445,118 B2 * | 5/2013 | Cordonier ............ B01J 21/066  428/457 |
| 8,492,581 B2 | 7/2013 | Frost et al. |
| 8,691,413 B2 | 4/2014 | Esswein et al. |
| 8,753,761 B2 | 6/2014 | Esswein et al. |
| 9,300,000 B2 | 3/2016 | Jansen et al. |
| 9,382,274 B2 | 7/2016 | Esswein et al. |
| 9,409,842 B1 | 8/2016 | Fu et al. |
| 2002/0177042 A1 | 11/2002 | Amendola |
| 2003/0068561 A1 | 4/2003 | Okahara et al. |
| 2003/0143456 A1 | 7/2003 | Kazacos et al. |
| 2003/0228394 A1 | 12/2003 | Abdel-Monem et al. |
| 2004/0096746 A1 | 5/2004 | Wietelmann et al. |
| 2005/0098437 A1 | 5/2005 | Shiepe |
| 2005/0244707 A1 | 11/2005 | Skyllas-Kazacos et al. |
| 2006/0047094 A1 | 3/2006 | Cherkasov et al. |
| 2007/0275291 A1 | 11/2007 | Gu et al. |
| 2008/0274385 A1 | 11/2008 | Creeth |
| 2008/0292964 A1 | 11/2008 | Kazacos et al. |
| 2009/0110998 A1 | 4/2009 | Miyachi et al. |
| 2009/0130525 A1 | 5/2009 | Miyachi et al. |
| 2009/0208807 A1 | 8/2009 | Miyachi et al. |
| 2009/0308752 A1 | 12/2009 | Evans et al. |
| 2010/0003586 A1 | 1/2010 | Sahu |
| 2010/0059388 A1 | 3/2010 | Clarke et al. |
| 2010/0086823 A1 | 4/2010 | Koshino et al. |
| 2010/0086983 A1 | 4/2010 | Gellett et al. |
| 2010/0239946 A1 | 9/2010 | Miyachi et al. |
| 2011/0014532 A1 | 1/2011 | Knuckey et al. |
| 2011/0136016 A1 | 6/2011 | Huang et al. |
| 2011/0189549 A1 | 8/2011 | Sun et al. |
| 2011/0195283 A1 | 8/2011 | Sun et al. |
| 2011/0200890 A1 | 8/2011 | Kocherginsky |
| 2011/0223450 A1 | 9/2011 | Horne et al. |
| 2011/0244277 A1 | 10/2011 | Gordon, II et al. |
| 2011/0244367 A1 | 10/2011 | Watahiki et al. |
| 2012/0052347 A1 | 3/2012 | Wilson et al. |
| 2012/0077095 A1 | 3/2012 | Roumi et al. |
| 2012/0107661 A1 | 5/2012 | Lee et al. |
| 2012/0135278 A1 | 5/2012 | Yoshie et al. |
| 2012/0171541 A1 | 7/2012 | Park et al. |
| 2012/0183868 A1 | 7/2012 | Toussaint et al. |
| 2012/0196188 A1 | 8/2012 | Zhang et al. |
| 2012/0202099 A1 | 8/2012 | Perry et al. |
| 2012/0208061 A1 | 8/2012 | Sahu et al. |
| 2012/0244406 A1 | 9/2012 | Xia et al. |
| 2012/0263990 A1 | 10/2012 | Kim |
| 2013/0004819 A1 | 1/2013 | Mun et al. |
| 2013/0157087 A1 | 6/2013 | Pandy et al. |
| 2013/0252062 A1 | 9/2013 | Wilkins et al. |
| 2013/0252137 A1 | 9/2013 | Zhang et al. |
| 2014/0028260 A1 | 1/2014 | Goeltz et al. |
| 2014/0028261 A1 | 1/2014 | Esswein et al. |
| 2014/0030572 A1 | 1/2014 | Esswein et al. |
| 2014/0030573 A1 | 1/2014 | Esswein et al. |
| 2014/0030631 A1 | 1/2014 | Esswein et al. |
| 2014/0051003 A1 | 2/2014 | Esswein et al. |
| 2014/0080035 A1 | 3/2014 | Esswein et al. |
| 2014/0138576 A1 | 5/2014 | Esswein et al. |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |
| 2014/0349177 A1 | 11/2014 | Chung et al. |
| 2014/0377666 A1 | 12/2014 | Kodama et al. |
| 2015/0236543 A1 | 8/2015 | Brushett et al. |
| 2015/0372333 A1 | 12/2015 | Odom et al. |

(56) References Cited

U.S. PATENT DOCUMENTS

| | | | |
|---|---|---|---|
| 2016/0066578 | A1 | 3/2016 | Ala'Aldeen et al. |
| 2016/0149251 | A1 | 5/2016 | Reece |
| 2016/0208165 | A1 | 7/2016 | Li et al. |
| 2016/0264603 | A1 | 9/2016 | Esswein et al. |
| 2016/0268623 | A1 | 9/2016 | Esswein et al. |
| 2016/0272659 | A1* | 9/2016 | King .................. C07F 7/28 |
| 2016/0276693 | A1 | 9/2016 | Goeltz et al. |
| 2016/0276694 | A1 | 9/2016 | Goeltz et al. |
| 2016/0276695 | A1 | 9/2016 | Esswein et al. |
| 2017/0253620 | A1 | 9/2017 | Humbarger et al. |
| 2017/0256811 | A1 | 9/2017 | Humbarger et al. |
| 2017/0271704 | A1 | 9/2017 | Morris-Cohen |
| 2018/0162886 | A1* | 6/2018 | Millard ................ H01M 8/188 |

FOREIGN PATENT DOCUMENTS

| | | |
|---|---|---|
| EP | 0814527 A2 | 12/1997 |
| EP | 1290068 A2 | 3/2003 |
| EP | 1411576 A1 | 4/2004 |
| EP | 1901379 A1 | 3/2008 |
| EP | 2235781 A1 | 10/2010 |
| EP | 2463950 A1 | 6/2012 |
| FR | 1533662 A | 7/1968 |
| GB | 1354886 A | 6/1974 |
| WO | WO-95/12219 A1 | 5/1995 |
| WO | WO-1997/017354 A1 | 5/1997 |
| WO | WO-2004/095602 A2 | 11/2004 |
| WO | WO-2006/135958 A1 | 12/2006 |
| WO | WO-2007/044852 A2 | 4/2007 |
| WO | WO-2007/101284 A1 | 9/2007 |
| WO | WO-2011/075135 A1 | 6/2011 |
| WO | WO-2011/098781 A1 | 8/2011 |
| WO | WO-2011/149624 A1 | 12/2011 |
| WO | WO-2012/075810 A1 | 6/2012 |
| WO | WO-2013/006427 A1 | 1/2013 |
| WO | WO-2013/048603 A1 | 4/2013 |
| WO | WO-2015/069439 A1 | 5/2015 |

OTHER PUBLICATIONS

Borgias et al "Synthetic, structural, and physical studies of titanium complexes of catechol and 3,5-di-tert-butylcatechol", Inorg. Chem. 1984, 23, 1009-1016. (Year: 1984).*
Chi et al "Structural characterization of Sr—Ti- and Ba—Ti catecholate complexes . . . ", Journal of Physics and Chemistry of Solids 62 (2001) 1871-1879. (Year: 2001).*
Wang et al., "Issues in Freeze Drying of Aqueous Solutions," Chinese Journal of Chemical Engineering, 2012, 20(3), pp. 551-559.
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Borgias, "Synthetic, structural, and physical studies of titanium complexes of catechol and 3,5-di-tert-butylcatechol," Inorg. Chem., Apr. 1984, 23(8), 1009-1016.
Bosch et al., "Novel Catalysis of Hydroquinone Autoxidation with Nitrogen Oxides," J. Org. Chem., 1994, pp. 2529-2536, 59.
Brezina, "Study of the reduction of oxygen on a carbon paste electrode in an alkaline medium," Coll. Czech. Chem. Commun., 1973, 38(10), 3024-3031.
Caulton, "Systematics and Future Projections Concerning Redox-Noninnocent Amide/Imine Ligands," Eur. J. Inorg. Chem., Jan. 2012, 2012(3), 435-443.
Cerofontain et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107.
Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.

Cohen, "The Association of Ferrocyanide Ions With Various Cations," J. Phys. Chem., Aug. 1957, 61(8), 1096-1100.
Davies, "Eiectroceramics from Source Materials via Molecular Intermediates: PbTiO3 from Ti02 via [Ti(catecholate)3]2-," J. Am. Ceram. Soc., Aug. 1990, 73(8), 2570-2572.
Davies, "Electroceramics from Source Materials via Molecular Intermediates: BaTiO3 from Ti02 via [Ti(catecholate)3]2-," May 1990, J. Am. Ceram. Soc., Aug. 1990, 73(5), 1429-30.
Dehaen et al, "A Self-Assembled Complex with a Titanium (IV) Catecholate Core as a Potential Bimodal Contrast Agent," Chem Eur J, 2012, pp. 293-302, vol. 18.
Fryda, "Wastewater Treatment With Diamond Electrodes," Diamond Materials, Electrochemical Society Proceedings, 2000, 99(32), 473-483.
Gail, "Cyano Compounds, Inorganic" in Ullmann's Encyclopedia of Industrial Chemistry, 2012, 10, 674-710.
Hollandsworth, "Zinc/Ferrocyanide Battery Development Phase IV" Lockheed Missiles and Space Company, Inc., Contractor report, Sandia Contract DE-AC04-76DP00789, May 1985, 278 pages.
Kim, "Novel catalytic effects of Mn3O4 for all vanadium redox flow batteries," Chem. Commun., Apr. 2012, 48(44), 5455-5457.
Kulesza, "Electrochemical preparation and characterization of hybrid films composed of Prussian blue type metal hexacyanoferrate and conducting polymer," Electrochimica Acta, Aug. 2001, 46(26-27), 4065-4073.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom Suillus tridentinus (Boletales)," Eur. J. Org. Chem., 2008, pp. 816-825.
Leung, "An undivided zinc--cerium redox flow battery operating at room temperature (295 K)," Electrochemistry Communications, 2011, vol. 13, pp. 770-773.
Leung, "Ce(III)/Ce(iV) in methanesulfonic acid as the positive half cell of a redox flow battery," Electrochimica Acta, 2011, vol. 56, pp. 2145-2153.
Leung, "Characterization of a zinc-cerium flow battery," Journal of Power Sources, 2011, vol. 195, pp. 5174-5185.
Leung, "Development of a Zinc-Cerium Redox Flow Battery", 2011, 352 pages.
Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.
Maison, et al., "Effect of Calcination Temperature on Phase Transformation and Particle size of Barium Titanate Fine Powders Synthesized by the Catecholate Process," ScienceAsia, 2001, pp. 239-243, 27.
McOmie et al. "The Thiele-Winter Acetoxylation of Quinones," Organic Reactions, 1972, pp. 199-277, 19, John Wiley and Sons, Inc., New York.
Modiba, "Electrochemical impedance spectroscopy study of Ce(IV) with aminopolycarboxylate ligands for redox flow batteries applications," Journal of Power Sources, May 2012, vol. 205, 1-9.
Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.
Modiba, "Electrolytes for redox flow battery systems," Dissertation presented for the degree of Doctor of Philosophy Chemistry at the University of Stellenbosch, Department of Chemistry and Polymer Science, Mar. 2010.
Murakami et al., "The Chelating Behavior of Catechol-4-sulfonate with Iron(III) Ion," Bulletin of the Chemical Society of Japan, 1963, pp. 1408-1411; vol. 36.
Nguyen, "Flow Batteries," The Electrochemical Society Interface, Fall2010, 19(3), 54-56.
Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.

(56) References Cited

OTHER PUBLICATIONS

Raymond, "Coordination isomers of biological iron transport compounds. VI. Models of the enterobactin coordination site. A crystal field effect in the structure of potassium tris(catecholato)chromate(III) and —ferrate(III) sesqu ihydrates, K3[M(02C6H4)3]. 1 . 5H2O, M=chromium, iron," J. Am. Chem. Soc., Mar. 1976, 98(7), 1767-1774.

Saito et al. "DPPH radical-scavenging reaction of protocatechuic acid: differnce in reactivity between acids and their esters," Helv Chim Acta, 2006, pp. 1395-1407, vol. 89.

Sever et al, "Visible absorption spectra of metal-catecholate and metal-tironate complexes," Dalton Trans., pp. 1061-1072, 2004.

Sigma-Aldrich Tris(hydroxymethyl)aminomethane, 2015.

Soloveichik, "Flow Batteries: Current Status and Trends," 2015, Chem. Rev., 115 (20), pp. 11533-11558.

Sommer, "Titanium (IV) complexes with ligands having oxygen donor atoms in aqueous solutions," Zeitschrift fur Anorganische und Aligemeine Chemie, Mar. 1963, pp. 191-197, vol. 321, issue 3-4.

Spyroudis, "Hydroxyquinones: Synthesis and Reactivity," Molecules, 2000, pp. 1291-1330, 5.

Steenken, "One-electron redox potentials of phenols. Hydroxy- and aminophenols and related compounds of biological interest," J. Phys. Chem., Sep. 1982, 86(18), 3661-3667.

Torres-Gomez, "Energy Storage in Hybrid Organic-Inorganic Materials Hexacyanoferrate-Doped Polypyrrole as Cathode in Reversible Lithium Cells," J. of The Electrochemical Society, 2000, 147(7), 2513-2516.

Trant, "Solubility of Sodium Ferrocyanide and Potassium Ferrocyanide in Solutions of NaOH and KOH Mixtures at 25.degree. C.," University of Rochester, The David T. Kearns Center, Xerox Undergraduate Research Fellows Program, Jul. 28, 2011, 1 page.

Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.

Wang, "Determination of iron, titanium, osmium, and aluminum with tiron by reversephase high performance liquid chromatography/electrochemistry," Microchem. J., Jun. 1991, 43(3), 191-197.

Weber, "Redox flow batteries: a review," Journal of Applied Electrochemistry, Oct. 2011, 41(10), 1137-1164.

Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.

Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.

Devi et al., "pH-metric investigation on Mixed-Ligand Complexs of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.

Xu, "Mechanics of metal-catecholate complexes: The roles of coordination state and metal types," Scientific Reports, Oct. 10, 2013, 3:2914, pp. 1-7.

Vliet et al., "Hydroxyhydroquinone Triacetate," Organic Synthesys, 1941, Coll vol. 1, p. 317 (1941), vol. 4, p. 35 (1925) 3 pages.

International Search Report and Written Opinion dated Jan. 19, 2017 from International Application No. PCT/US16/58433.

International Search Report and Written Opinion dated Feb. 17, 2017 from International Application No. PCT/US16/65159.

Ahluwalia et al., Intermediates for Organic Synthesis, Chapter 1, Phenols, Sections 1.21 and 1.23, 2003, I.K. International Pvt. Ltd.

Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.

IUPAC Compendium of Chemical Terminology, "coordinatively unsaturated complex," 1997, http://old.iupac.org/goldbook/C01334.pdf.

Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.

International Search Report and Written Opinion from PCT/US17/14764, dated Apr. 20, 2017.

International Search Report and Written Opinion from PCT/US16/69190, dated May 3, 2017.

International Search Report and Written Opinion from PCT/US2017/022203, dated Jun. 6, 2017.

* cited by examiner

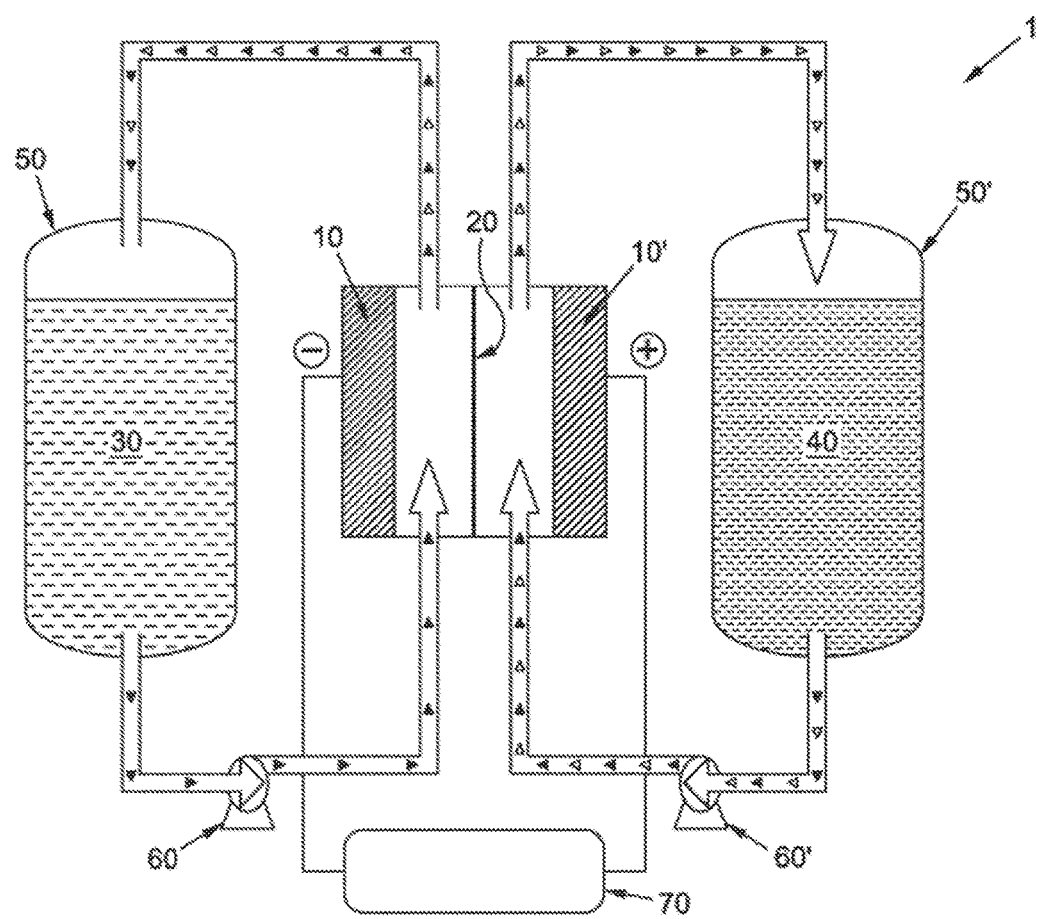

NEAT METHODS FOR FORMING TITANIUM CATECHOLATE COMPLEXES AND ASSOCIATED COMPOSITIONS

CROSS-REFERENCE TO RELATED APPLICATIONS

Not applicable.

STATEMENT REGARDING FEDERALLY SPONSORED RESEARCH OR DEVELOPMENT

Not applicable.

FIELD

The present disclosure generally relates to energy storage and, more specifically, to methods for synthesizing titanium catecholate complexes as active materials for use in energy storage systems.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination complexes for this purpose. As used herein, the terms "coordination complex," "coordination compound," "metal-ligand complex," or simply "complex" synonymously refer to a compound having at least one covalent bond formed between a metal center and a donor ligand. The metal center can cycle between an oxidized form and a reduced form in an electrolyte solution, where the oxidized and reduced forms of the metal center represent states of full charge or full discharge depending upon the particular half-cell in which the coordination complex is present. In certain instances, additional electrons can be transferred through the oxidation or reduction of one or more of the molecules constituting the ligands.

Titanium complexes can be particularly desirable active materials for use in flow batteries and other electrochemical energy storage systems, since such metal complexes can provide good half-cell potentials (e.g., less than −0.3 V) and current efficiencies exceeding 85% at high current density values (e.g., greater than 100 mA/cm$^2$). Various titanium catecholate complexes can be especially desirable active materials in this regard, since they are relatively stable complexes and have a significant degree of solubility in aqueous media. Although various methods are available for synthesizing titanium catecholate complexes (also referred to herein as titanium catechol complexes, titanium catecholate coordination compounds, catechol complexes of titanium, and/or similar terms), none are presently viable for producing the significant quantities of these complexes needed to support commercial-scale energy storage applications. In addition, residual solvents from currently employed syntheses of titanium catecholate complexes can become incorporated in aqueous electrolyte solutions in which the complexes are present, which can be undesirable in various instances. Certain residual organic solvents, for example, can cause membrane swelling in a flow battery, which can compromise the flow battery's operation. In addition, residual organic solvents can present environmental or safety concerns in some instances.

In addition, titanium catecholate complexes are usually synthesized in a salt form for incorporation in aqueous electrolyte solutions. In such salt forms, the titanium catecholate complex itself bears a formal negative charge and one or more positively charged counterions are present to maintain charge balance. If extraneous salts (i.e., salts not associated with the titanium catecholate complex) are also present in an aqueous electrolyte solution, the solubility of the complex can be undesirably lowered through a common ion effect. Since most conventional syntheses of titanium catecholate complexes liberate at least one byproduct species that can readily lead to extraneous salt formation, it can be difficult to realize maximized solubility levels for these complexes. The decreased solubility values can undesirably impact energy density values and other parameters of interest.

In view of the foregoing, improved methods for synthesizing titanium catecholate complexes to support their use as active materials in energy storage applications would be highly desirable in the art. The present disclosure satisfies the foregoing needs and provides related advantages as well.

SUMMARY

In various embodiments, methods for synthesizing coordination complexes containing titanium are described herein, particularly titanium catecholate complexes. The methods can include: combining a catechol compound and a titanium reagent in an absence of solvent to product a reaction mixture, and reacting the titanium reagent with the catechol compound in a neat state to form a titanium catecholate complex containing at least one catecholate ligand.

In other various embodiments, methods for synthesizing titanium catecholate complexes can include: combining a catechol compound and a titanium reagent in an absence of solvent to produce a reaction mixture, reacting the titanium reagent with the catechol compound in a neat state to form a titanium catecholate complex containing at least one catecholate ligand, separating a byproduct species including a hydrogen halide gas from the titanium catecholate complex, and after separating the byproduct species, reacting a base with the titanium catecholate complex to produce a salt form titanium catecholate complex. The titanium reagent is in a liquid state while reacting with the catechol compound.

In still other various embodiments, compositions of the present disclosure can include: an aqueous phase, and a salt form titanium catecholate complex dissolved in the aqueous phase and containing at least one catecholate ligand. The compositions are substantially free of organic solvents and extraneous salts in the aqueous phase that are not associated with the salt form titanium catecholate complex. Flow batteries containing the compositions in at least one electrolyte solution are also described herein.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

The Drawing shows a schematic of an illustrative flow battery.

DETAILED DESCRIPTION

The present disclosure is directed, in part, to flow batteries and compositions containing salt form titanium catecholate complexes, particularly alkali metal salt forms, that are free or substantially free of extraneous salts and organic solvents. The present disclosure is also directed, in part, to methods for synthesizing titanium catecholate complexes via neat syntheses.

The present disclosure may be understood more readily by reference to the following description taken in connection with the accompanying Drawing and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable on a large scale while maintaining high efficiency values can be extremely desirable. Flow batteries employing coordination complexes as active materials have generated significant interest in this regard. Exemplary description of illustrative flow batteries, their use, and operating characteristics is provided hereinbelow. Titanium coordination complexes, particularly those containing at least one catecholate ligand, can be especially desirable due to their favorable half-cell potentials and high current efficiency values, among other factors. Although various techniques are presently available in the art for synthesizing titanium catecholate complexes, none are believed to be suitable for producing high-purity active materials at the very large (multi-pound up to multi-ton) scales needed to support commercial energy storage applications. Raw material costs, labor expenses, low yields and insufficient purity are among the factors that can be problematic at present for supplying commercially viable quantities of these types of active materials. Other metal complexes containing alternative metal centers and/or ligands differing from catecholate ligands can be similarly problematic in this regard.

As used herein, the term "catechol" refers to a compound having an aromatic ring bearing hydroxyl groups on adjacent carbon atoms (i.e., 1,2-hydroxyl groups). Optional substitution can also be present in addition to the 1,2-hydroxyl groups. As used herein, the term "catecholate" refers to a substituted or unsubstituted catechol compound that is bound to a metal center via a metal-ligand bond, particularly a titanium metal center. As used herein, the term "unsubstituted catecholate" refers to the particular case where 1,2-dihydroxybenzene (catechol) is bound to a metal center via a metal-ligand bond. The optional substitution on catecholate ligands can serve a number of purposes such as, for example, altering the solubility characteristics and/or half-cell potentials of the metal complexes that they produce. Monosulfonated catecholate ligands, for example, can improve the solubility of titanium coordination complexes while maintaining desirable electrochemical properties that are at least comparable to those obtained when only unsubstituted catecholate ligands are present. As used herein, the term "monosulfonated" refers to one sulfonic acid group or any salt thereof being present on an aromatic ring. Catecholate ligands bearing an additional hydroxyl group, such as pyrogallol, 1,2,4-trihydroxybenzene and gallic acid, for example, can be similarly advantageous in this regard. Catecholates such as the foregoing can also be optionally further substituted. Other advantageous catecholate ligands bearing further substitution are discussed hereinbelow. It is to be understood that catechols and catecholates suitable for use in the present disclosure also include positional isomers that are not necessarily specifically illustrated herein. In addition, monosubstituted catechols and catecholates can also be polysubstituted in some embodiments, particularly disubstituted or trisubstituted, unless otherwise indicated herein.

Conventional syntheses of titanium coordination complexes, including titanium catecholate complexes, are conducted in an organic solvent or an aqueous solvent. These syntheses can be problematic in several respects. Although frequently used, organic solvents can present particular issues. When organic solvents are used during the syntheses of titanium coordination complexes, residual organic solvent can be retained by the titanium coordination complexes and become incorporated in an aqueous electrolyte solution. Residual organic solvent in an aqueous electrolyte solution can contact a flow battery's membrane or separator and result in swelling, which can undesirably compromise the flow battery's operation. Organic solvents also add to the cost of fabricating a flow battery, and organic solvents can further produce undesirable environmental impacts. In addition, both organic and aqueous solvents can retain byproduct species that, if not properly managed, can lead to extraneous salt formation upon producing a salt form of the titanium coordination complexes, thereby reducing purity and potentially impacting other factors such as solubility.

The present inventors discovered processes for synthesizing titanium catecholate complexes that can proceed from readily available and relatively inexpensive starting materials and take place in a neat state. As used herein, the terms "neat" and "neat state" refer to the condition of solvent being absent or excluded from a reaction mixture. Surprisingly, the direct combination of various titanium reagents and one or more catechol compounds can react in good yields in the absence of solvent to form titanium catecholate complexes, which can be further processed into salt form titanium catecholate complexes. Liquid state titanium reagents can be particularly desirable in this regard. Since the syntheses described herein take place without using a solvent, they avoid the cost and operational issues that can be encountered when organic solvents are used in conventional syntheses. Moreover, by conducting neat syntheses of titanium catecholate complexes and directly forming a solid product in a reaction vessel, byproduct species generated during the reaction can be easily removed before converting the initially produced titanium catecholate complexes into a desired salt form.

More specifically, the neat syntheses described herein take place using readily available titanium (IV) reagents such as titanium tetrahalides and titanium oxyhalides. Related titanium (IV) alkoxide reagents can also be used in some embodiments. Liquid titanium reagents (e.g., titanium tetrachloride) or low-melting titanium reagents (i.e., m.p.<150° C., such as titanium tetrabromide or titanium tetraiodide) can be especially desirable, since they result in a high degree of contact with the one or more catechol compounds to better promote complex formation. However, even solid titanium reagents can be suitably used in some instances, such as when liquid or low-melting catechol compounds are used.

Moreover, titanium tetrahalide and titanium oxyhalide reagents can be particularly desirable for use in neat syntheses since they generate highly volatile hydrogen halide gases upon their reaction with catechol compounds and other ligatable materials. The hydrogen halide gas can be substantially removed from the initially formed titanium catecholate complex (e.g., by pumping and/or flowing an inert gas) prior to producing a salt form titanium catecholate complex via the addition of a base. If not removed, a hydrogen halide gas can react with the added base to produce extraneous salt when converting the titanium catecholate complex into a desired salt form and/or lead to incomplete conversion of the initially produced titanium catecholate complex into the desired salt form. For flow batteries, an especially desirable salt form can be an alkali metal salt form in some embodiments, although alternative salt forms can also be suitable, as discussed below. Accordingly, neat syntheses of titanium catecholate complexes allow some of the more troubling issues associated with producing these complexes to be substantially averted in a simultaneous manner.

Further, syntheses and further processing of the titanium catecholate complexes can be conducted on a wide range of scales, ranging from gram-scale laboratory processes up to multi-ton production, advantageously without isolating a solid material at any stage in many cases. Because the syntheses described herein generate one or more removable byproduct species, salt form titanium catecholate complexes can be obtained with good purity levels in high-concentration aqueous phases that can be suitable for use in flow batteries and other electrochemical energy storage systems with little to no further processing. In particular, the syntheses described herein allow the titanium catecholate complexes to be produced in an aqueous phase without forming significant amounts of extraneous salts, such as extraneous alkali metal halide salts, that are not associated with the titanium catecholate complexes in their desired salt form. That is, the syntheses described herein do not produce a substantial amount of additional salt co-product when forming the salt form titanium catecholate complexes. The syntheses described herein can limit the formation of extraneous salts through judicious removal of the byproduct species generated when initially forming the titanium catecholate complexes. If not removed, the byproduct species, in some cases, can react to form the extraneous salts and can complicate the stoichiometry of base addition.

Since the initially generated titanium catecholate complex is synthesized from a reaction mixture lacking solvents, removal of volatile byproduct species can occur much more readily than when analogous syntheses take place in the presence of a solvent. A solvent, when present, can retain the byproduct species. As such, the neat syntheses described herein can be advantageous in terms of attaining higher purity levels once the titanium catecholate complexes have been converted into a desired salt form in an aqueous electrolyte solution. For example, HCl and other hydrogen halide gases, which can form as a byproduct of the reaction when halide-containing titanium reagents are used, can be effectively driven off to substantial completion from the neat reaction mixture before forming an aqueous phase containing the salt form titanium catecholate complex. In addition, the neat syntheses described herein can be advantageous through decreasing synthesis costs by eliminating solvents and mitigating their environmental impact.

Byproduct species, such as HCl and other hydrogen halides, if they remain present when converting a titanium catecholate complex to a desired salt form, can be exceedingly detrimental. As discussed above, hydrogen halides can react with the bases used in conjunction with converting the titanium catecholate complexes into a salt form and thereby generate extraneous salts. The extraneous salts generated upon reaction of the base with the byproduct species can be detrimental due to their propensity to decrease solubility of the salt form titanium catecholate complexes through a common ion effect. In addition, the reaction between the byproduct species and the base can prevent the initially formed catecholate complex from being completely converted into its desired salt form.

In some embodiments, the initially formed titanium catecholate complex can be converted into an alkali metal salt form titanium catecholate complex through reaction with an alkali metal base, particularly using an alkaline aqueous solution. As used herein, the term "alkali metal" refers to a metal in Group I of the periodic table, such as lithium, sodium or potassium. Sodium, potassium, or mixed sodium/potassium salt forms can be particularly desirable salt forms for incorporation in an electrolyte solution of a flow battery. Although alkali metal salt form titanium catecholate complexes can be advantageous for use in conjunction with the components of flow batteries and other electrochemical systems, it is to be recognized that alternative salt forms can be synthesized using other bases. For example, alkaline earth metal salt form titanium catecholate complexes can be synthesized by using an alkaline earth metal base, such as calcium hydroxide. Other salt forms, such as ammonium, phosphonium, sulfonium, tetraalkylammonium, tetraarylammonium, mixed alkyl and aryl tetrasubstituted ammonium, tetraarylphosphonium, iminium, and nitronium salt forms, for example, can also be prepared and used similarly. Mixed salt forms, which can desirably have improved aqueous phase solubility in some cases, are also possible in some embodiments of the present disclosure.

As referenced above, minimal workup is generally needed when practicing the neat syntheses of the present disclosure. Namely, after initially forming the titanium catecholate complexes and removing the byproduct species through pumping or inert gas flow, no further purification or manipulation is generally necessary before combining the base to produce the corresponding salt form titanium catecholate complexes. Reactions with additional ligatable materials can sometimes occur when producing the salt form titanium catecholate complexes. Because minimal workup is needed, production runs can provide large quantities of aqueous phase product in a relatively short amount of time. Accordingly, the syntheses described herein are readily amenable to scale up to a desired level. Further, the syntheses described herein can be readily extended to continuous modes of operation, rather than batchwise processes.

Although titanium catecholate complexes can be advantageous for use in the further applications described herein, other metal catecholate complexes can also be suitably produced via similar neat syntheses and incorporated in flow batteries and other electrochemical energy storage systems. Metal catecholate complexes containing alternative metals such as, for example, Al, Ca, Co, Cr, Sr, Cu, Fe, Hf, Mg, Mn, Mo, Ni, Pd, Pt, Ru, Sn, Zn, Zr, V, W and U can be synthesized through similar procedures and utilized as the active material for a flow battery, particularly starting from liquid state metal-containing reagents. Lanthanide and actinide reagents that are reactive with catechol compounds can also be suitable in this regard. Like titanium, zirconium and hafnium coordination compounds can possess highly desirable properties when utilized as an active material in a flow battery. Accordingly, the disclosure herein directed to titanium can be extended to the foregoing alternative metals without limitation by one having ordinary skill in the art.

Furthermore, the disclosure herein can also be extended to titanium and other metal coordination complexes that contain only catecholate ligands, combinations of one or more catecholate ligands with other non-catecholate ligands, or only non-catecholate ligands. Suitable non-catecholate ligands can include any of monodentate, bidentate or tridentate ligands, some examples of which are provided hereinbelow. Bidentate ligands can be especially desirable since they complex metal centers in a similar manner to catechol compounds and can serve as a direct replacement thereof. The disclosure herein can also be extended to monohydroxybenzene compounds (i.e., phenolate ligands) in some embodiments.

In various embodiments, the present disclosure describes methods including: combining a catechol compound and a titanium reagent in an absence of solvent to produce a reaction mixture, and reacting the titanium reagent with the catechol compound in a neat state to form a titanium catecholate complex containing at least one catecholate ligand. As used herein, the term "titanium reagent" refer to any chemical compound containing titanium.

As indicated above, a byproduct species is also generated when reacting the titanium reagent with the catechol compound to form the titanium catecholate complex. As used herein, the term "byproduct species" refers to any chemical compound that is not a coordination complex, particularly a titanium coordination complex. In particular embodiments, the byproduct species can be one or more hydrogen halides, which can be readily expelled from the reaction mixture as the titanium catecholate complex forms. Accordingly, in some embodiments, the methods of the present disclosure can further include separating the byproduct species from the titanium catecholate complex. Suitable techniques for separating the byproduct species are discussed hereinafter.

As also indicated above, the initially produced titanium catecholate complex can be converted into a desired salt form through its reaction with a base. Accordingly, the methods of the present disclosure can further include reacting a base with the titanium catecholate complex to produce a salt form titanium catecholate complex. In more particular embodiments, the base can be reacted with the titanium catecholate complex after separating the byproduct species, thereby minimizing or eliminating the production of extraneous salt upon converting the initially produced titanium catecholate complex into its salt form. In still more particular embodiments, the salt form titanium catecholate complex can be produced in an aqueous phase. As such, in some embodiments, the aqueous phase can be substantially free of an extraneous salt not associated with the salt form titanium catecholate complex. As used herein, the term "substantially free of an extraneous salt" refers to about 0.01 molar equivalents or less of the extraneous salt being present relative to the salt form titanium catecholate complex.

In still more specific embodiments, the base can be present in an alkaline aqueous solution when being combined with the titanium catecholate complex. Accordingly, in such embodiments, the methods of the present disclosure allow for the salt form titanium catecholate complex to be produced directly in an aqueous phase. In some embodiments, the salt form titanium catecholate complex can be at least partially soluble in the aqueous phase. In alternative embodiments, the methods can include combining a solid base or a liquid base with the titanium catecholate complex, separately adding water or another aqueous solution, or vice versa, and reacting the base with the titanium catecholate complex to again produce the salt form titanium catecholate complex in an aqueous phase, which can be substantially free of an extraneous salt in various embodiments. Additional disclosure regarding suitable bases is provided hereinbelow.

The aqueous phase containing the salt form titanium catecholate complex can be substantially free of byproducts formed before or during the production of the salt form titanium catecholate complex, such as metal halides or other extraneous salts, as discussed herein. For example, in the case of the base being an alkali metal base, the aqueous phase can be substantially free of extraneous alkali metal halide salts. The extraneous salts can be formed from a reaction between anions introduced from the titanium reagent and cations introduced from the base used to generate the salt form titanium catecholate complexes. As such, in more specific embodiments, the aqueous phase can be substantially free of extraneous salts having the same cation as the salt form titanium catecholate complexes.

Accordingly, in some or other specific embodiments, methods of the present disclosure can include: separating a byproduct species from the titanium catecholate complex, where the byproduct species (e.g., one or more hydrogen halides) is generated when reacting the titanium reagent with the catechol compound; after separating the byproduct species, combining an alkaline aqueous solution containing a base with the titanium catecholate complex; and reacting the base with the titanium catecholate complex to produce a salt form titanium catecholate complex that is at least partially dissolved in an aqueous phase. In further embodiments, the aqueous phase is substantially free of an extraneous salt not associated with the salt form titanium catecholate complex.

Catechol compounds suitable for use in the various embodiments described herein are not considered to be particularly limited. In some embodiments, the catechol compound can be o-catechol itself (i.e., unsubstituted 1,2-dihydroxybenzene). In some or other embodiments, the catechol compound can include at least one substituted catechol compound, which can optionally be present in combination with an unsubstituted catechol compound. Accordingly, the initially produced titanium catecholate complexes and salt form titanium catecholate complexes described herein can include unsubstituted catecholate ligands, substituted catecholate ligands, or any combination thereof. In further embodiments, additional ligands that are non-catecholate in nature can also be present in combination with substituted or unsubstituted catecholate ligands. As referenced above, non-catecholate ligands and other metals can also be used in alternative embodiments of the present disclosure. In particular embodiments, 3,4-dihydroxybenzenesulfonic acid can be an especially desirable substituted catechol compound for use in forming a salt form titanium catecholate complex. Pyrogallol, 1,2,4-trihydroxybenzene and gallic acid are also substituted catechol compounds that can be particularly desirable. These and other similar catechol compounds can be further substituted in some embodiments.

Other examples of substituted catechol compounds that can be suitable for use in the embodiments described herein can include those bearing solubilizing groups to increase the aqueous solubility of the resulting complexes. Non-limiting examples of substituted catechol compounds that can be suitable for use in the embodiments described herein can include those having a structure of

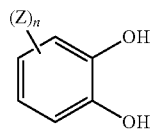

in a neutral form or a salt form. Z is a heteroatom functional group selected from the group consisting of $A^1R^{A1}$, $A^2R^{A2}$, $A^3R^{A3}$, CHO, and sulfonic acid. Variable n is an integer ranging between 1 and 4, such that one or more Z are bound to the substituted catechol compound at an open aromatic ring position. Each Z is the same or different when more than one Z is present. $A^1$ is —$(CH_2)_a$— or —$(CHOR)(CH_2)_a$—, $R^{A1}$ is —$OR^1$ or —$(OCH_2CH_2O)_bR^1$, a is an integer ranging between 0 and about 6, and b is an integer ranging between 1 and about 10. $A^2$ is —$(CH_2)_c$— or —$CH(OR^2)(CH_2)_d$—, $R^{A2}$ is —$NR^3R^4$, a carbon-linked amino acid, or —$C(=O)XR^5$, X is —O— or —$NR^6$—, c is an integer ranging between 0 and about 6, and d is an integer ranging between 0 and about 4. $A^3$ is —O— or —$NR^2$—, $R^{A3}$ is —$(CHR^7)_eOR^1$, —$(CHR^7)_eNR^3R^4$, —$(CHR^7)_eC(=O)XR^5$, or —$C(=O)(CHR^7)_fR^8$, e is an integer ranging between 1 and about 6, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —$(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —$(OCH_2CH_2O)_bR^1$. In some embodiments, substituted catechol compounds of the structure shown above can be covalently bonded to another such structure, each of which can be independently substituted with $(Z)_n$ as set forth above. Such structures can be joined to one another a single bridging group or a double bridging group.

The titanium catecholate complexes of the present disclosure contain titanium in the +4 oxidation state. The most common coordination number of titanium (IV) is 6. As such, the titanium catecholate complexes of the present disclosure can accommodate at most five other ligands when at least one catecholate ligand is present, and at most four other additional ligands when the at least one catecholate ligand is bound in a bidentate manner. Moreover, when the titanium catecholate complexes contain only catecholate ligands, or one or more catecholate ligands in combination only with other bidentate ligands, the titanium catecholate complexes can contain at most three bidentate ligands in total.

As indicated above, the initially produced titanium catecholate complex can be converted, typically without isolation or further purification, into a salt form titanium catecholate complex through reaction with a base, such as an alkali metal base or other suitable base. Bearing the coordination properties of titanium (IV) and catecholate ligands in mind, the salt form titanium catecholate complexes of the present disclosure are believed to have a formula of $$D_{1-6}Ti(L)_3,$$

wherein D is metal cation, ammonium cation, tetraalkylammonium cation, or phosphonium cation and L is one or more bidentatate ligands, where at least a portion of L is a catecholate ligand. The molar equivalents of D can range between 1 and 6 depending on whether D is a monovalent or divalent cation, and whether L contains any ionizable functional groups. For example, when D is a monovalent cation, such as an alkali metal ion, and L represents an uncharged catecholate ligand, 2 molar equivalents of the alkali metal ion are present to maintain charge balance (i.e., the salt form titanium catecholate complexes have a formula of $D_2Ti(L)_3$). When the base is not an alkali metal base, D can also include any alternative cations (e.g, a single alkaline earth metal ion, a mixture of alkaline earth metal ions, phosphonium ions, ammonium ions, tetralkylammonium ions, and the like), optionally in combination with one or more alkali metal ions, in which case the molar equivalents of D actually present reflect the amount needed to maintain charge balance. In some embodiments, a single type of substituted or unsubstituted catecholate ligand can be present in the complexes. In other embodiments, mixtures of two or more unsubstituted and/or substituted catecholate ligands can be present. In still other embodiments, ligands that are non-catecholate ligands can be present. For example, in some embodiments, the salt form titanium catecholate complexes can have a formula of $$D_{1-6}Ti(L_1)(L_2)(L_3),$$

wherein D is defined as above and $L_1$-$L_3$ are ligands, provided that at least one of $L_1$-$L_3$ is a catecholate ligand or a substituted catecholate ligand. In some specific embodiments, two catecholate ligands can be present, and in other specific embodiments, three catecholate ligands can be present. Alternative ligands that can constitute the balance of $L_1$-$L_3$ include, but are not limited to, certain exemplary ligands described hereinbelow. When at least one monodentate non-catecholate ligand is present, additional ligands beyond just three ligands (i.e., $L_1$, $L_2$ and $L_3$) can be present to an amount necessary to achieve a full coordination sphere.

In more specific embodiments, salt form titanium catecholate complexes of the present disclosure can have a formula of $$Na_mK_nLi_oTi(L)_3,$$

wherein m+n+o=2, provided that L does not bear a charged functional group, and L is defined as above. For example, in the case of at least one catecholate ligand (L) bearing a negatively charged functional group, such as a sulfonic acid anion, greater than two molar equivalents of lithium, sodium and/or potassium ions are needed to maintain charge balance. In more particular embodiments, o=0 and m+n=2, such that the salt form is a sodium and/or potassium salt form. In still more particular embodiments, both m and n are non-zero numbers, and they can be equal or non-equal to one another. In some embodiments, a ratio of m to n can range between about 1:10 to about 10:1, or between about 1:5 or about 5:1. In some embodiments, substantially equal molar quantities of sodium and potassium can be present in the salt form titanium catecholate complexes. Complexes having mixtures of sodium and potassium counterions can be desirable in terms of their potentially increased solubility in aqueous phases. As indicated above, non-catecholate ligands can also be present in such complexes.

Accordingly, in more general embodiments, the salt form titanium catecholate complexes disclosed herein can have a formula of $$D_{1-7}Ti(L_1)(L_2)(L_3)$$

where, in this case, D is a monovalent or divalent cation (e.g., an alkali metal cation, an alkaline earth metal cation, an ammonium cation, a tetraalkylammonium cation, a phosphonium ion, or other alternative cation), and $L_1$-$L_3$ are bidentate ligands, provided that at least one of $L_1$-$L_3$ is a catecholate ligand or a substituted catecholate ligand, and one or more of $L_1$-$L_3$ optionally bears a positive or negative charge. The molar equivalents of D that are present depend both upon the charge of D and the charge, if any, borne by $L_1$-$L_3$. In more particular embodiments, the salt form titanium catecholate complexes can have a formula of $$D_2Ti(L_1)(L_2)(L_3),$$

where, in this case, D is a monovalent cation or a mixture of monovalent cations, and $L_1$-$L_3$ are defined as above.

The salt form of the titanium catecholate complexes can depend upon the cation associated with the base used to promote formation of the salt form. Suitable bases are not considered to be particularly limited, provided that they have sufficient basicity to produce the salt form titanium catecholate complex. Suitable bases can include, for example, a metal hydroxide, a metal oxide, a metal bicarbonate, a metal carbonate, an ammonium base, a tetraalkylammonium base, a deprotonated ligand base, an amine, a borate, a metal borohydride, a metal hydride, a metal phosphate, a sulfonium base, a phosphazenium base, a guanidinium base, a metal azide, a cyanate base, a thiocyanate base, a metal carboxylate, a phenolate base, a carbamate base, an imide base, a deprotonated sulfonamide base, a nitroxyl base, a basic anion-exchange resin, a metal chalcogenide, a phosphonium base, a tetraalkylphosphonium base, a tetraarylphosphonium base, or any combination thereof. Although some of these bases produce salt form titanium catecholate complexes that are more soluble in an aqueous phase, others may be more beneficial for forming an organic phase containing the titanium catecholate complexes in their salt form.

In some embodiments of the present disclosure, the base can be an alkali metal base or combination of alkali metal bases. In some embodiments, the alkali metal base can include an alkali metal hydroxide such as sodium hydroxide, potassium hydroxide, or any combination thereof. In more particular embodiments, the alkali metal base can be a mixture of sodium hydroxide and potassium hydroxide. The molar ratios of the sodium hydroxide and potassium hydroxide can lie within the counterion ranges disclosed above.

Complexes having mixed sodium and potassium counterions can be especially desirable due to their potentially increased solubility values compared to those obtained when only a single alkali metal counterion is present.

In alternative embodiments of the present disclosure, alkali metal bases such as alkali metal oxides, alkali metal carbonates, and alkali metal bicarbonates can be used to convert the initially formed titanium catecholate complex into the salt form titanium catecholate complex. Optionally, these alkali metal bases can be used in combination with the alkali metal hydroxide bases discussed above. Again, a mixture of sodium and potassium counterions can be introduced through the choice of the alkali metal bases used to produce the salt form titanium catecholate complex. For example, an alkali metal hydroxide having a first alkali metal counterion can be combined with an alkali metal carbonate or bicarbonate having a second alkali metal counterion to accomplish the foregoing.

As still another alternative to alkali metal bases, ammonium bases, such as ammonium hydroxide, can also be used in some embodiments of the present disclosure. In some embodiments, the alkaline aqueous solution can contain a mixture of ammonium hydroxide and an alkali metal base, in which case the resulting salt form titanium catecholate complex can contain a mixture of ammonium and alkali metal counterions. Some ammonium cations can be alkyl substituted, such as tetraalkylammonium cations, and can be suitably incorporated in the salt form titanium catecholate complexes.

In some embodiments, ligands in addition to substituted or unsubstituted catecholate ligands can be present in the complexes described herein. Other ligands that can be present alternatively and/or in combination with catecholate ligands include, for example, amines, diamines, amino alcohols, amino acids, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that such ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Compositions such as glycols having a hydrocarbon backbone can optionally contain one or more double or triple carbon-carbon bonds. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of ligands that can be present in the complexes of the present disclosure can include monodentate, bidentate, and/or tridentate ligands. Examples of monodentate ligands that can be present in the complexes of the present disclosure include, for example, carbonyl or carbon monoxide, nitride, oxo, hydroxo, water, sulfide, thiols, pyridine, pyrazine, and the like. Examples of bidentate ligands that can be present in the complexes of the present disclosure include, for example, bipyridine, bipyrazine, ethylenediamine, diols (including ethylene glycol), and the like, any of which can contain optional carbon-carbon double or triple bonds. Examples of tridentate ligands that can be present in the complexes of the present disclosure include, for example, terpyridine, diethylenetriamine, triazacyclononane, tris(hydroxymethyl)aminomethane, and the like.

In some embodiments, suitable titanium reagents for use in the neat syntheses disclosed herein can include titanium tetrahalides and titanium oxyhalides. Suitable titanium tetrahalides can include titanium tetrachloride, titanium tetrabromide, titanium tetraiodide, and titanium mixed tetrahalides. As used herein, the term "titanium mixed tetrahalide" refers to a titanium tetrahalide containing two or more different halides, such as $TiCl_3Br$, $TiCl_2Br_2$ and $TiClBr_3$. These titanium reagents are all molecular compounds and can readily react according to the embodiments described herein, since they are either liquids or low-melting solids. Titanium tetrafluoride and the related $TiF_6^{2-}$ complex anion are extended polymeric solids and can react with catechol compounds and other ligatable substances less readily. Titanium tetrafluoride and $TiF_6^{2-}$ generate hydrogen fluoride upon reacting with ligatable compounds, which can be especially problematic to address from a manufacturing standpoint due to the high reactivity and toxicity of this hydrogen halide gas. However, even titanium tetrafluoride and the $TiF_6^{2-}$ complex anion can also be suitable for use in some instances. Titanocene dichloride and titanium oxysulfate can also be suitable titanium reagents in some embodiments of the present disclosure.

Suitable titanium oxyhalide reagents can include titanium oxychloride ($TiOCl_2$), titanium oxybromide ($TiOBr_2$) and titanium oxyiodide ($TiOI_2$). The related titanium oxyfluoride compound ($TiOF_2$) can present similar handing and toxicity issues as titanium tetrafluoride, although it can also be used suitably in some instances. Although titanium oxyhalide reagents are higher melting compounds, they can react suitably in some instances with liquid or molten catechol compounds in the neat reaction mixture.

Other suitable titanium reagents can include titanium (IV) alkoxides. These titanium reagents have the advantage of not producing a byproduct species that can undergo a reaction to form extraneous salts upon converting the initially produced titanium catecholate complex into its salt form. Instead, the reaction of these titanium reagents with a catechol compound or other ligatable compound produces an alcohol as a byproduct. In some embodiments, the alcohol byproduct can be separated from the initially produced titanium catecholate complex in a similar manner to that discussed above for hydrogen halides. In other embodiments, the alcohol byproduct can be retained while converting the initially produced titanium catecholate complex into its desired salt form, in which case it can become incorporated in an aqueous phase containing the salt form titanium catecholate complex. Alternately, the alcohol byproduct can be removed from the aqueous phase after incorporating the salt form titanium catecholate complex therein.

Titanium tetrahalides, titanium mixed tetrahalides, and titanium oxyhalides react to release a hydrogen halide gas as a byproduct species upon contacting a ligatable compound, such as a catechol compound. The hydrogen halide byproduct species can be readily removed from the reaction mixture as a gas, as discussed hereinbelow. As discussed above, substantial removal of the hydrogen halide allows the salt form titanium catecholate complex to be formed in an aqueous phase without generating an appreciable amount of extraneous salts through reacting the hydrogen halide with the base added to produce the salt form. Avoiding the production of extraneous salts, such as alkali metal halide salts, can be desirable for improving solubility of the salt form titanium catecholate complexes in an aqueous phase being utilized as an electrolyte solution in a flow battery, for example.

In some embodiments, the titanium reagent can be present in a liquid state while reacting with the catechol compound. Liquid state titanium reagents can be especially desirable for use in the neat syntheses disclosed herein due to their ability to attain a high degree of contact with the catechol compound. In some embodiments, titanium tetrachloride can be a particularly suitable liquid state titanium reagent. Low melting solid titanium reagents, such as titanium tetrabromide and titanium tetraiodide, can also be similarly desirable in this respect. In some or other embodiments, various liquid state titanium alkoxide reagents, such as titanium ethoxide, titanium propoxide, titanium isopropoxide, and titanium t-butoxide, for example, can be suitable titanium reagents.

Accordingly, in some embodiments, the titanium reagent used to form the titanium catecholate complex can be at least one titanium compound that is a liquid at 25° C. In some or other embodiments, suitable titanium reagents can also include at least one titanium compound that has a melting point of about 150° C. or below In alternative embodiments, solid titanium reagents can be used in combination with liquid catechol compounds or catechol compounds that are melted or undergo melting during the reaction to produce the titanium catecholate complex. Combining a solid titanium reagent with a liquid state catechol compound can again result in good contact between the reactants for promoting formation of the complex.

In some embodiments, the neat syntheses disclosed herein can further include heating the reaction mixture to promote the reaction between the titanium reagent and the catechol compound. In other embodiments, the reaction mixture need not necessarily be heated for the reaction to occur. Since the reaction mixture can be suitably heated, titanium reagents and/or catechol compounds that melt upon heating the reaction mixture can also be used suitably in some embodiments of the present disclosure. Heating of the reaction mixture can take place at a temperature of above 25° C. and less than about 50° C., or less than about 75° C., or less than about 100° C., or less than about 125° C., or less than about 150° C. Accordingly, in some embodiments, the titanium reagent used to form the titanium catecholate complex can be at least one titanium compound that is a solid that liquefies upon being heated to a temperature at which the titanium catechol complex still forms. In this regard, suitable titanium reagents can have a melting point of about 50° C. or less, or about 75° C. or less, or about 100° C. or less, or about 125° C. or less, or about 150° C. or less. Titanium tetrabromide (m.p.=50° C.) and titanium tetraiodide (m.p.=150° C.) can be desirable titanium reagents in this regard. Even when a titanium reagent and/or a catechol compound is/are a liquid at 25° C., heating of the reaction mixture can still be desirable in some instances.

Due to volatility issues of either the titanium reagent and/or the catechol compound, heating of the reaction mixture can take place in a sealed reaction vessel in some embodiments. When the reaction takes place in a sealed reaction vessel, the byproduct species can be vented upon the completion of the reaction before producing the salt form titanium catecholate complex. In other embodiments, the byproduct species can be removed continuously or semi-continuously during the reaction.

In some embodiments, the reaction mixture can be maintained at a reduced pressure after initially forming the titanium catecholate complex and before reacting the base therewith. As used herein, the term "reduced pressure" refers to any pressure below normal atmospheric pressure, which is 760 torr at sea level. In some embodiments, suitable reduced pressures for removing HCl gas or other hydrogen halides from the reaction mixture can range between about 50 torr and about 400 torr, or between about 100 torr and about 200 torr.

In some or other embodiments, flowing inert gas can contact the reaction mixture after initially forming the titanium catecholate complex and before reacting the base therewith. Suitable inert gases can include, for example, nitrogen, helium, argon, neon, or the like. Similar to the reduced pressure operations discussed above, the flowing inert gas can promote removal of hydrogen halide gases or other volatile byproducts from the reaction mixture.

In some embodiments, the initially formed titanium catecholate complex can be isolated from the reaction mixture prior to generating the salt form titanium catecholate complex. Isolation of the initially formed titanium catecholate complex can facilitate removal of any hydrogen halide byproducts that are not removed during the neat synthesis. Non-volatile byproducts, if present, can also be removed during this stage. In some embodiments, isolation and optional purification can involve contacting the initially formed titanium catecholate complex with a washing solvent, followed by filtration, centrifugation, decantation, and the like. More desirably, however, the initially formed titanium catecholate complex is not contacted with a solvent in the course of its being isolated from the reaction mixture. Avoiding contact with solvents can help preserve the benefits of conducting a neat synthesis, such as those discussed above.

Even more desirably, however, the initially formed titanium catecholate complex is not isolated from the reaction mixture. As such, the methods of the present disclosure can include combining an alkaline aqueous solution or base with the initially formed titanium catecholate complex without isolating the complex and generating the corresponding salt form. Advantageously, this avoids having to remove and handle solids from the reaction vessel. Furthermore, reacting the initially formed titanium catecholate complex without isolation can help avoid introducing trace or non-trace quantities of residual solvents into the aqueous phase upon generating the salt form titanium catecholate complex. Therefore, in more specific embodiments, the initially formed titanium catecholate complex and the salt form titanium catecholate complex can be formed consecutively in a single reaction vessel.

Accordingly, in some embodiments, methods of the present disclosure can include: combining a catechol compound and a titanium reagent in an absence of solvent to form a reaction mixture; reacting the titanium reagent with the catechol compound in a neat state to form a titanium catecholate complex containing at least one catecholate ligand; separating a byproduct species including a hydrogen halide gas from the titanium catecholate complex; and after separating the byproduct species, reacting a base with the titanium catecholate complex to produce a salt form titanium catecholate complex. In more specific embodiments, the base can be present in an alkaline aqueous solution and the salt form titanium catecholate complex can be produced in an aqueous phase.

In some embodiments, combining the catechol compound and the titanium reagent can include adding the titanium reagent to the catechol compound. When adding the titanium reagent to the catechol compound, the titanium reagent can be added portionwise, continuously, or substantially all at once. The ability to add the titanium reagent substantially all at once can be advantageous compared to solvent-based syntheses, wherein extreme reactivity can necessitate a slower addition of the titanium reagent. In other embodiments, combining the catechol compound and the titanium reagent can include adding the catechol compound to the titanium reagent.

An amount of base in the alkaline aqueous solution can be chosen such that it is sufficient to convert the titanium catecholate complex into its corresponding salt form in an aqueous phase without forming extraneous salts, including situations where excess base itself can be an extraneous salt. In particular embodiments, the amount of base can be chosen to be stoichiometrically equivalent to that of the titanium reagent initially present, or the base can be present in a slight stoichiometric excess or deficit. Accordingly, the resulting aqueous phase containing the salt form titanium catecholate complex can be neutral, modestly basic or modestly acidic, depending upon the actual amount of base that is present and the yield at which the titanium catecholate complex is initially formed. Upon separating base-consuming byproduct species from the reaction mixture, such as HCl gas or other hydrogen halides, essentially none of the base reacts to form unwanted extraneous salts in the aqueous phase. Further, since the titanium catecholate complex is formed in high yields, a good estimate of the aqueous phase pH can be obtained based upon the initial molar amount of titanium reagent that is present and the molar equivalents of added base.

In more particular embodiments, an amount of base in the alkaline aqueous solution is such that the aqueous phase containing the salt form titanium catecholate complex has an initial pH of about 6 to about 8. In still more particular embodiments, an amount of the base can be chosen such that the resulting aqueous phase has a pH of about 7 to about 8. Attaining an initial pH that is not far removed from neutral allows the salt form titanium catecholate complex to be formed and maintained in the aqueous phase under pH conditions where it is relatively stable. In addition, an initial pH within this range can be readily adjusted upwardly without introducing extraneous salts, such as alkali metal halides, to the aqueous phase, as described hereinafter. That is, by forming an aqueous phase having a near-neutral pH at which the salt form titanium catecholate complex is stable, more careful upward pH adjustment can then take place afterward. In contrast, if excess base was added when generating the salt form titanium catecholate complex, the initial pH would be higher. Although the salt form titanium catecholate complex might well be stable at this higher pH, the pH could not be lowered with an acid without introducing extraneous salts in the aqueous phase. For example, in the case of an alkali metal base being present in the alkaline aqueous solution, lowering the initial pH with hydrochloric acid would result in the unwanted production of alkali metal chloride salts, such as sodium chloride or potassium chloride, within the aqueous phase, which can be desirable to avoid for the reasons noted above. Accordingly, in some embodiments, the initial pH can be adjusted by adding an additional quantity of the alkaline aqueous solution or base to adjust the pH to a range of about 9 to about 10, or about 10 to about 12, or about 12 to about 14. The pH range can be chosen depending upon the particular application in which the aqueous phase is to be employed.

In various embodiments of the present disclosure, the aqueous phase containing the salt form titanium catecholate complex can have a concentration of the complex of about 0.5 M or above. In more particular embodiments, the concentration of the salt form titanium catecholate complex can range between about 0.5 M and about 2 M, or between about 0.75 M and about 1.5 M or between about 1 M and about 2 M.

Therefore, in some or other various embodiments, the present disclosure provides compositions containing salt form titanium catecholate complexes. In more specific embodiments, the compositions described herein can include an aqueous phase, and a salt form titanium catecholate complex dissolved in the aqueous phase and containing at least one catecholate ligand, such as an alkali metal salt form. The compositions can contain an aqueous phase in which the aqueous phase is free or substantially free of organic solvents and that are also free or substantially free of extraneous salt not associated with the salt form titanium catecholate complex. In more specific embodiments, the compositions can contain an aqueous phase that are free of organic solvents and in which about 0.01 molar equivalents or less of extraneous salts relative to the salt form titanium catecholate complex are present. In more specific embodiments, the aqueous phase can be substantially free of alkali metal halide salts, particularly sodium chloride or potassium chloride, while the salt form titanium catecholate complex is an alkali metal salt form. As discussed above, the neat synthetic processes described hereinabove allow aqueous phases of this type to be readily prepared. The organic solvent that is excluded from the aqueous phase can be that which was used in conjunction with forming the initially produced titanium catecholate complex.

In some embodiments, the aqueous phase can be free of organic solvents and consist of water alone as a solvent for the salt form titanium catecholate complex. In other embodiments of the present disclosure, the aqueous phase can contain at least about 98% water by weight. In other more specific embodiments, the aqueous phase can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight.

In further embodiments, the aqueous phase can include a viscosity modifier, a wetting agent, a buffer, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous phase can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Illustrative buffers that can be present include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof inclusion of any of these components in the aqueous phase can help maintain the salt form titanium catecholate complex in a dissolved form and/or facilitate the incorporation of the aqueous phase in a flow battery, for example.

In some embodiments, the aqueous phases described herein can further include one or more mobile ions (i.e., an extraneous electrolyte) for use as an electrolyte solution in a flow battery or similar electrochemical system. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5%, or less than about 2% of the mobile ions can constitute protons, hydronium, or hydroxide. In other various embodiments, aqueous phases containing the salt form titanium catecholate complexes of the present disclosure can lack an extraneous electrolyte altogether.

As indicated above, the salt form titanium catecholate complexes of the present disclosure, particularly alkali metal salt form titanium catecholate complexes, and related aqueous phases containing these complexes can be incorporated in flow batteries and related electrochemical systems. Further disclosure on suitable flow batteries and their operating parameters follows hereinafter.

In various embodiments, flow batteries of the present disclosure can include a first half-cell containing a first electrolyte solution therein, in which the first electrolyte solution constitutes a composition of the present disclosure with an aqueous phase and a salt form titanium catecholate complex produced by a neat synthesis incorporated in the aqueous phase. More specific discussion regarding the salt form titanium catecholate complexes and their associated compositions is provided above.

In further embodiments, flow batteries of the present disclosure can also include a second half-cell having a second electrolyte solution therein, where the second electrolyte solution contains an active material differing from that in the first electrolyte solution. In more specific embodiments, the second electrolyte solution can be an aqueous solution containing an iron hexacyanide complex. Iron hexacyanide complexes can be particularly desirable active materials due to their facile electrode kinetics and substantially reversible electrochemical behavior within the working electrochemical window of aqueous solutions. Nitroxide compounds (particularly [2,2,6,6-tetramethyl-4-(sulfooxy)piperidin-1-yl]oxidanyl or salt, or a pyrroline, pyrrolidine, imidazoline, imidazolidine, oxazoline, oxazolidine, thiazoline, thioazolidine, and their benzo-fused analogues, and derivatives thereof) can be similarly advantageous active materials for the second electrolyte solution in some embodiments. Hence, these substances can allow high open circuit potentials and cell efficiencies to be realized, particularly in combination with a salt form titanium catecholate complex as the active material in the first electrolyte solution. In more specific embodiments, flow batteries of the present disclosure can include the first electrolyte solution in contact with a negative electrode of the flow battery and the second electrolyte solution in contact with the positive electrode of the flow battery.

Illustrative flow battery configurations will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the aqueous phases described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolyte solutions. The first aqueous electrolyte solution can be an aqueous phase containing a salt form titanium catecholate complex defining a composition of the present disclosure, as described above. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions; (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination complex; (b) second aqueous electrolyte solution containing a second coordination complex or nitroxide compound; (c) a separator positioned between said first and second aqueous electrolyte solutions; and (d) an optional mobile ion in the first and second aqueous electrolyte solutions. As described in more detail below, the separator can be an ionomer membrane, and it can have a thickness of less than 100 microns and have an associated net charge that is the same sign as that of the first and second coordination complexes.

The Drawing depicts a schematic of an illustrative flow battery containing a single electrochemical cell. Although the Drawing shows a flow battery containing a single electrochemical cell, approaches for combining multiple electrochemical cells together are known and are discussed in brief hereinbelow. Unlike typical battery technologies (e.g., Li-ion, Ni-metal hydride; lead-acid, and the like), where active materials and other components are housed in a single assembly, flow batteries transport (e.g., via pumping) redox-active energy storage materials from storage tanks through an electrochemical stack. This design feature decouples the electrical energy storage system power from the energy storage capacity, thereby allowing for considerable design flexibility and cost optimization.

As shown in the Drawing, flow battery 1 includes an electrochemical cell that features separator 20 (e.g., a membrane) that separates the two electrodes 10 and 10' of the electrochemical cell. As used herein, the terms "separator" and "membrane" synonymously refer to an ionically conductive and electrically insulating material disposed between the positive and negative electrodes of an electrochemical cell. Electrodes 10 and 10' are formed from a suitably conductive material, such as a metal, carbon, graphite, and the like. Although the Drawing has shown electrodes 10 and 10' as being spaced apart from separator 20, electrodes 10 and 10' can also be abutted with separator 20 in more particular embodiments. The materials) forming electrodes 10 and 10' can be porous, such that they have a high surface area for contacting first electrolyte solution 30 and second electrolyte solution 40, the active materials of which are capable of cycling between an oxidized state and a reduced state during operation of flow battery 1. For example, one or both of electrodes 10 and 10' can be formed from a porous carbon cloth or a carbon foam in particular embodiments.

Pump 60 affects transport of first electrolyte solution 30 containing a first active material from tank 50 to the electrochemical cell. The flow battery also suitably includes second tank 50' that holds second electrolyte solution 40 containing a second active material. The second active material in second electrolyte solution 40 can be the same material as the first active material in first electrolyte solution 30, or it can be different. Second pump 60' can affect transport of second electrolyte solution 40 to the electrochemical cell. Pumps (not shown in the Drawing) can also be used to affect transport of the first and second electrolyte solutions 30 and 40 from the electrochemical cell back to tanks 50 and 50'. Other methods of affecting fluid transport, such as siphons, for example, can also suitably transport first and second electrolyte solutions 30 and 40 into and out of the electrothemical cell. Also shown in the Drawing is power source or load 70, which completes the circuit of the electrochemical cell and allows a user to collect or store electricity during its operation. Connection to the electrical grid for charging or discharging purposes can also occur at this location.

It should be understood that the Drawing depicts a specific, non-limiting embodiment of a flow battery. Accordingly, flow batteries consistent with the spirit of the present disclosure can differ in various aspects relative to the configuration of the Drawing. As one example, a flow battery system can include one or more active materials that are solids, gases, and/or gases dissolved in liquids. Active materials can be stored in a tank, in a vessel open to the atmosphere, or simply vented to the atmosphere.

During operation of a flow battery in a charging cycle, one of the active materials undergoes oxidation and the other active material undergoes reduction. In a discharging cycle, the opposite processes occur in each half-cell. Upon changing the oxidation states of the active materials, the chemical potentials of the electrolyte solutions are no longer in balance with one another. To relieve the chemical potential imbalance, dissolved mobile ions migrate through the separator to lower the charge in one electrolyte solution and to raise the charge in the other electrolyte solution. Thus, the mobile ions transfer the charge generated upon oxidizing or reducing the active materials, but the mobile ions themselves are not usually oxidized or reduced. To maintain facile electrode kinetics, the flow batteries are configured such that the mobile ions and the active materials remain continuously dissolved in the electrolyte solutions. In addition, by keeping the mobile ions and the active materials continuously dissolved in the electrolyte solutions, potential issues associated with circulating solids can be averted.

As indicated above, multiple electrochemical cells can also be combined with one another in an electrochemical stack in order to increase the rate that energy can be stored and released during operation. The amount of energy released is determined by the overall amount of active materials that are present. An electrochemical stack utilizes bipolar plates between adjacent electrochemical cells to establish electrical communication but not fluid communication between the two cells across the bipolar plate. Thus, bipolar plates contain the electrolyte solutions in an appropriate half-cell within the individual electrochemical cells. Bipolar plates are generally fabricated from electrically conductive materials that are fluidically non-conductive on the whole. Suitable materials can include carbon, graphite, metal, or a combination thereof. Bipolar plates can also be fabricated from non-conducting polymers having a conductive material dispersed therein, such as carbon particles or fibers, metal particles or fibers, graphene, and/or carbon nanotubes. Although bipolar plates can be fabricated from the same types of conductive materials as can the electrodes of an electrochemical cell, they can lack the continuous porosity permitting an electrolyte solution to flow completely through the latter. It should be recognized that bipolar plates are not necessarily entirely non-porous entities, however. Bipolar plates can have innate or designed flow channels that provide a greater surface area for allowing an electrolyte solution to contact the bipolar plate. Suitable flow channel configurations can include, for example, interdigitated flow channels. In some embodiments, the flow channels can be used to promote delivery of an electrolyte solution to an electrode within the electrochemical cell.

In some instances, an electrolyte solution can be delivered to and withdrawn from each electrochemical cell via a fluid inlet manifold and a fluid outlet manifold (not shown in the Drawing). In some embodiments, the fluid inlet manifold and the fluid outlet manifold can provide and withdraw an electrolyte solution via the bipolar plates separating adjacent electrochemical cells. Separate manifolds can provide each electrolyte solution individually to the two half-cells of each electrochemical cell. In more particular embodiments, the fluid inlet manifold and the fluid outlet manifold can be configured to supply and withdraw the electrolyte solutions via opposing lateral faces of the bipolar plates (e.g. by supplying and withdrawing the electrolyte solution from opposing ends of the flow channels of the bipolar plate).

As used herein, the terms "separator" and "membrane" refer to an conically conductive and electrically insulating, material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent; and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—CF=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, polyvinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination complex, the average diameter of the coordination complex can be about 50% greater than the average pore size of the porous membrane. On the other hand, if a porous membrane has substantially uniform pore sizes, the average diameter of the coordination complex can be about 20% larger than the average pore size of the porous membrane. Likewise, the average diameter of a coordination complex is increased when it is further coordinated with at least one water molecule. The diameter of a coordination complex of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator liar; a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm². In further embodiments, suitable separators can include those in which the flow battery is capable of operating at a voltage efficiency of greater than 70%, greater than 80% or even greater than 90%.

The diffusion rate of the first and second active materials through the separator can be less than about $1 \times 10^{-5}$ mol cm$^{-2}$ day$^{-1}$, or less than about $1 \times 10^{-6}$ mol cm$^{-2}$ day$^{-1}$, or less than about $1 \times 10^{-7}$ mol cm$^{-2}$ day$^{-1}$, or less than about $1 \times 10^{-9}$ mol cm$^{-2}$ day$^{-1}$, or less than about $1 \times 10^{-11}$ mol cm$^{-2}$ day$^{-1}$, or less than about $1 \times 10^{-13}$ mol cm$^{-2}$ day$^{-1}$, or less than about $1 \times 10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range of the negative operating potential of the system, such that the resulting oxidized or reduced form of the first active material has the same charge sign (positive or negative) as the first active material and the ionomer membrane also has a net ionic charge of the same sign; and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). In some embodiments, the net ionic charge in both the oxidized and reduced forms can be negative. The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" refers to the amount of ions passing through the ionomer membrane, balancing the charge associated with the flow of external electricity/electrons. That is, the flow battery is capable of operating or operates with the substantial exclusion of the active materials by the ionomer membrane, and such exclusion can be promoted through charge matching.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where the round trip current efficiency is greater than about 70%, greater than about 80%, or greater than about 90% (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 μm, less than about 75 μm, less than about 50 μm, or less than about 250 μm; (f) where the flow battery is capable of operating at a current density of greater than about 100 mA/cm² with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software which may include safety systems); and a power conditioning unit. The flow battery cell stack accomplishes the conversion of charging and discharging cycles and determines the peak power. The storage tanks contain the positive and negative active materials, such as the coordination complexes disclosed herein, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" refers to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad \text{(Equation 1)}$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad \text{(Equation 2)}$$

where [active materials] is the molar concentration of the active material in either the negative or positive electrolyte, whichever is lower, and N is the number of electrons transferred per molecule of active material. The related term "charge density" refers to the total amount of charge that each electrolyte contains. For a given electrolyte, the charge density can be calculated by Equation 3

$$\text{Charge density} = (26.8 \text{ A-h/mol}) \times [\text{active material}] \times N \quad \text{(Equation 3)}$$

where [active material] and N are as defined above.

As used herein, the term "current density" refers to the total current passed in an electrochemical cell divided by the geometric area of the electrodes of the cell and is commonly reported in units of $mA/cm^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-ting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\% \quad \text{(Equation 4)}$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

A 5-L 5-neck round-bottom flask was equipped with an overhead stirrer, nitrogen inlet, a glass addition funnel, thermometer, and an efficient reflux condenser equipped with a gas outlet connected to an HCl scrubber. The flask was charged with 429.4 g of catechol (3.9 mol, 1.95 equivalents) and 245.8 g pyrogallol (1.95 moles, 0.97 equivalents). The addition funnel was charged with 220 mL of neat titanium (IV) chloride (2 mol, 1.00 equivalents) via cannula transfer from a sealed bottle. Directly preceding the titanium (IV) chloride addition to the reaction mixture, the nitrogen flow was turned off, since the evolution of HCl gas maintained the flask under positive pressure. The neat titanium (IV) chloride was added over approximately 20 minutes. The initial drops of $TiCl_4$ reacted with the catechol/pyrogallol solids and imparted a dark tinge to the reaction mixture while releasing HCl gas. The reaction mixture was then heated to 130° C. for 2-3 hours. While hot, 10 ml of $H_2O$ was added to the reaction mixture, and heating was continued for an additional 2 hours. At 100° C., 700 mL of deionized water was added followed by heating for an additional 1 hour.

A solution of 6 M aqueous base (3 M NaOH/3 M KOH) was separately sparged with nitrogen for 1 hour. The base solution (800 mL) was added to the initially formed complex slurry over the course of 3 minutes with stirring. The final solution pH value was approximately 10.5. The basic solution was then stirred for an additional 1 hour while heating, at which time there was no sign of solids in the aqueous phase or on the flask walls.

The solution was then filtered through a 0.45 micron filter and analyzed further. UV-VIS spectroscopy showed $\varepsilon_{380\ nm} = 10{,}860\ M^{-1}\ cm^{-1}$. $^1H$ and $^{13}C$ NMR spectroscopy were consistent with complex formation.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
   combining a catechol compound and a titanium reagent in an absence of solvent to produce a reaction mixture; and
   reacting the titanium reagent with the catechol compound in a neat state to form a titanium catecholate complex comprising at least one catecholate ligand.

2. The method of claim 1, further comprising:
   separating a byproduct species from the titanium catecholate complex, the byproduct species being generated when reacting the titanium reagent with the catechol compound.

3. The method of claim 2, further comprising:
   reacting a base with the titanium catecholate complex to produce a salt form titanium catecholate complex.

4. The method of claim 3, wherein the base is reacted with the titanium catecholate complex after separating the byproduct species.

5. The method of claim 3, wherein the salt form titanium catecholate complex is produced in an aqueous phase.

6. The method of claim 5, wherein the base is present in an alkaline aqueous solution.

7. The method of claim 6, wherein the aqueous phase is substantially free of an extraneous salt not associated with the salt form titanium catecholate complex.

8. The method of claim 2, wherein the byproduct species comprises one or more hydrogen halides.

9. The method of claim 1, further comprising
reacting a base with the titanium catecholate complex to produce a salt form titanium catecholate complex.

10. The method of claim 9, wherein the salt form titanium catecholate complex is produced in an aqueous phase.

11. The method of claim 10, wherein the base is present in an alkaline aqueous solution.

12. The method of claim 1, further comprising:
separating a byproduct species from the titanium catecholate complex, the byproduct species being generated when reacting the titanium reagent with the catechol compound;
after separating the byproduct species, combining an alkaline aqueous solution comprising a base with the titanium catecholate complex; and
reacting the base with the titanium catecholate complex to produce a salt form titanium catecholate complex that is at least partially dissolved in an aqueous phase.

13. The method of claim 12, wherein the byproduct species comprises one or more hydrogen halides.

14. The method of claim 12, wherein the aqueous phase is substantially free of an extraneous salt not associated with the salt form titanium catecholate complex.

15. The method of claim 1, further comprising:
heating the reaction mixture.

16. The method of claim 1, wherein the titanium reagent comprises at least one titanium compound that is a liquid at 25° C.

17. The method of claim 1, wherein the titanium reagent comprises at least one titanium compound having a melting point of about 150° C. or below.

18. The method of claim 1, wherein combining the catechol compound and the titanium reagent comprises adding the titanium reagent to the catechol compound.

19. A method comprising:
combining a catechol compound and a titanium reagent in an absence of solvent to form a reaction mixture;
reacting the titanium reagent with the catechol compound in a neat state to form a titanium catecholate complex comprising at least one catecholate ligand;
wherein the titanium reagent is in a liquid state while reacting with the catechol compound;
separating a byproduct species comprising a hydrogen halide gas from the titanium catecholate complex; and
after separating the byproduct species, reacting a base with the titanium catecholate complex to produce a salt form titanium catecholate complex.

20. The method of claim 19, wherein the base is present in an alkaline aqueous solution and the salt form titanium catecholate complex is produced in an aqueous phase.

21. The method of claim 20, wherein the aqueous phase is substantially free of an extraneous salt not associated with the salt form titanium catecholate complex.

22. The method of claim 19, further comprising:
heating the reaction mixture.

* * * * *

UNITED STATES PATENT AND TRADEMARK OFFICE
CERTIFICATE OF CORRECTION

PATENT NO. : 10,320,023 B2
APPLICATION NO. : 15/435235
DATED : June 11, 2019
INVENTOR(S) : Millard et al.

It is certified that error appears in the above-identified patent and that said Letters Patent is hereby corrected as shown below:

On the Title Page

Item [56], replace:
"Chi et al "Structural characterization of Sr-Ti- and Ba-Ti catecholate complexes ...", Journal of Physics and Chemistry of Solids 62 (2001) 1871-1879. (Year: 2001).*" with --Chi et al "Structural characterization of Sr-Ti- and Ba-Ti catecholate complexes: Single source precursors for SrTiO3 and BaTiO3 binary oxides ", Journal of Physics and Chemistry of Solids 62 (2001) 1871-1879. (Year: 2001).*--

"Cerofontain et al. "Sulfonation and sulfation on reaction of 1,2-dihydroxybenzene and its methyl ethers in concentrated aqueous sulfuric acid," Reel Tray Chim Pays-Bas, 1988, pp. 325-330, vol. 107." with --Cerofontain et al. "Sulfonation and sulfation on reaction of 1,2-dihydroxybenzene and its methyl ethers in concentrated aqueous sulfuric acid," Reel Trav Chim Pays-Bas, 1988, pp. 325-330, vol. 107.--

"Davies, "Electrocerarnics from Source Materials via Molecular Intermediates: BaTI03 from TI02 via [TI (catecholate)3]2-," May 1990, J. Am. Cerarn. Soc., Aug. 1990, 73(5), 1429-30." with --Davies, "Electroceramics from Source Materials via Molecular Intermediates: BaTIO3 from TIO2 via [TI(catecholate)3] 2-," May 1990, J. Am. Cerarn. Soc., Aug. 1990, 73(5), 1429-30--

"Davies, "Eiectroceramics from Source Materials via Molecular Intermediates: PbTi03 from Ti02 via [Ti (catecholate)3]2-," J. Am. Ceram. Soc., Aug. 1990, 73(8), 2570-2572." with --Davies, "Electroceramics from Source Materials via Molecular intermediates: PbTiO3 from TiO2 via [Ti(catecholate)3]2-," J. Am. Ceram. Soc., Aug. 1990, 73(8), 2570-2572.--

"Kim, "Novel catalytic effects of Mn304 for all vanadium redox flow batteries," Chem. Commun., Apr. 2012, 48 (44), 5455-5457." with --Kim, "Novel catalytic effects of Mn3O4 for all vanadium redox flow batteries," Chem. Commun., Apr. 2012, 48(44), 5455-5457.--

Signed and Sealed this
Fifth Day of November, 2019

Andrei Iancu
*Director of the United States Patent and Trademark Office*

"Raymond , "Coordination isomers of biological iron transport compounds. VI. Models of the enterobactin coordination site. A crystal field effect in the structure of potassium tris(catecholato)chromate( III) and -ferrate ( III) sesq u ihyd rates, K3[M( 02C6H4 )3]. 1 . 5H20, M=chromium, iron," J. Am. Chem. Soc., Mar. 1976, 98(7), 1767-1774." with --Coordination isomers of biological iron transport compounds. VI. Models of the enterobactin coordination site. A crystal field effect in the structure of potassium tris(catecholato)chromate(III) and -ferrate(III) sesquihydrates, K3[M(O2C6H4)3].cntdot.1.5H2O, M = chromium, iron," J. Am. Chem. Soc., Mar. 1976, 98(7), 1767-1774.--